US00PP27719P3

(12) United States Plant Patent
Volmary

(10) Patent No.: US PP27,719 P3
(45) Date of Patent: Feb. 28, 2017

(54) ***FUCHSIA* PLANT NAMED 'VOLFUC 6054'**

(50) Latin Name: *Fuchsia×hybrida*
Varietal Denomination: VOLFUC 6054

(71) Applicant: Hubertus Volmary, Muenster (DE)

(72) Inventor: Hubertus Volmary, Muenster (DE)

(73) Assignee: Volmary GmbH, Muenster (DE)

( * ) Notice: Subject to any disclaimer, the term of this patent is extended or adjusted under 35 U.S.C. 154(b) by 43 days.

(21) Appl. No.: 14/545,624

(22) Filed: May 29, 2015

(65) Prior Publication Data

US 2016/0353639 P1 Dec. 1, 2016

(51) Int. Cl.
*A01H 5/02* (2006.01)

(52) U.S. Cl.
USPC ..... Plt./300

(58) Field of Classification Search
USPC ..... Plt./300
See application file for complete search history.

*Primary Examiner* — Keith Robinson
(74) *Attorney, Agent, or Firm* — C. A. Whealy

(57) ABSTRACT

A new and distinct cultivar of *Fuchsia* plant named 'VOLFUC 6054', characterized by its relatively compact, mounding to trailing plant habit; freely branching habit, dense and bushy plant form; moderately vigorous growth habit; freely flowering habit; and light red purple and violet blue-colored flowers.

2 Drawing Sheets

Botanical designation: *Fuchsia×hybrida.*
Cultivar denomination: 'VOLFUC 6054'.

BACKGROUND OF THE INVENTION

The present invention relates to a new and distinct cultivar of *Fuchsia* plant botanically known as *Fuchsia×hybrida* and hereinafter referred to by the name 'VOLFUC 6054'.

The new *Fuchsia* plant is a product of a planned breeding program conducted by the Inventor in Muenster, Germany. The objective of the breeding program is to create new compact and freely branching *Fuchsia* plants with numerous attractive flowers.

The new *Fuchsia* plant originated from a cross-pollination made by the Inventor in 2009 in Muenster, Germany of two unidentified proprietary selections of *Fuchsia×hybrida*, not patented. The new *Fuchsia* plant was discovered and selected by the Inventor as a single flowering plant within the progeny of the stated cross-pollination in a controlled greenhouse environment in Muenster, Germany in 2010.

Asexual reproduction of the new *Fuchsia* plant by terminal vegetative cuttings in a controlled environment in Muenster, Germany since 2010 has shown that the unique features of this new *Fuchsia* plant are stable and reproduced true to type in successive generations.

SUMMARY OF THE INVENTION

Plants of the new *Fuchsia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'VOLFUC 6054'. These characteristics in combination distinguish 'VOLFUC 6054' as a new and distinct *Fuchsia* plant:

1. Relatively compact, mounding to trailing plant habit.
2. Freely branching habit, dense and bushy plant form.
3. Moderately vigorous growth habit.
4. Freely flowering habit.
5. Light red purple and violet blue-colored flowers.

The new *Fuchsia* plant can be compared to plants of the female parent selection. Plants of the new *Fuchsia* differ primarily from plants of the female parent selection in the following characteristics:

1. Plants of the new *Fuchsia* are more mounding than and not as trailing as plants of the female parent selection.
2. Plants of the new *Fuchsia* are more freely flowering than plants of the female parent selection.
3. Plants of the new *Fuchsia* and the female parent selection differ in flower color as plants of the female parent selection have pink and white-colored flowers.

The new *Fuchsia* plant can be compared to plants of the male parent selection. Plants of the new *Fuchsia* differ primarily from plants of the male parent selection in the following characteristics:

1. Plants of the new *Fuchsia* are more mounding than and not as upright as plants of the male parent selection.
2. Plants of the new *Fuchsia* are more freely flowering than plants of the male parent selection.
3. Plants of the new *Fuchsia* and the male parent selection differ in flower color as plants of the male parent selection have blue and white-colored flowers.

Plants of the new *Fuchsia* can be compared to plants of *Fuchsia* 'Kiefuzak', disclosed in U.S. Plant Pat. No. 13,764. In side-by-side comparisons conducted in Muenster, Germany, plants of the new *Fuchsia* and 'Kiefuzak' differed in the following characteristics:

1. Plants of the new *Fuchsia* were slightly taller than plants of 'Kiefuzak'.
2. Plants of the new *Fuchsia* were not as pendulous as plants of 'Kiefuzak'.
3. Plants of the new *Fuchsia* were more freely branching than plants of 'Kiefuzak'.
4. Plants of the new *Fuchsia* had smaller leaves than plants of 'Kiefuzak'.

5. Plants of the new *Fuchsia* and 'Kiefuzak' differed in flower color as plants of 'Kiefuzak' had light red and purple-colored flowers.

BRIEF DESCRIPTION OF THE PHOTOGRAPHS

The accompanying colored photographs illustrate the overall appearance of the new *Fuchsia* plant showing the colors as true as it is reasonably possible to obtain in colored reproductions of this type. Colors in the photographs may differ slightly from the color values cited in the detailed botanical description which accurately describe the colors of the new *Fuchsia*.

The photograph on the first sheet is a top perspective view of a typical flowering plant of 'VOLFUC 6054' grown in a container.

The photograph on the second sheet is a close-up view of a typical flowering plant of 'VOLFUC 6054' grown in a container.

DETAILED BOTANICAL DESCRIPTION

The aforementioned photographs and following observations, measurements and values describe plants grown during the spring in 12-cm containers in a glass-covered greenhouse in Muenster, Germany and under cultural practices typically used in commercial production. During the production of the plants, day temperatures ranged from 18° C. to 20° C., night temperatures ranged from 15° to 18° C. and light levels ranged from 5,000 to 40,000 lux. Plants were pinched one time and were six months old when the photographs and the description were taken. In the following description, color references are made to The Royal Horticultural Society Colour Chart, 2005 Edition, except where general terms of ordinary dictionary significance are used.

Botanical classification: *Fuchsia×hybrida* 'VOLFUC 6054'.

Parentage:

*Female, or seed, parent*.—Unidentified proprietary selection of *Fuchsia×hybrida*, not patented.

*Male, or pollen, parent*.—Unidentified proprietary selection of *Fuchsia×hybrida*, not patented.

Propagation:

*Type*.—By vegetative terminal cuttings.

*Time to initiate roots, summer*.—About one to two weeks at temperatures ranging from 20° C. to 25° C.

*Time to initiate roots, winter*.—About two to three weeks at temperatures ranging from 15° C. to 23° C.

*Time to produce a rooted plant, summer*.—About three weeks at temperatures ranging from 20° C. to 25° C.

*Time to produce a rooted plant, winter*.—About 30 days at temperatures ranging from 15° C. to 23° C.

*Root description*.—Fine, fibrous.

*Rooting habit*.—Freely branching; medium density.

Plant description:

*Plant and growth habit*.—Relatively compact, upright and mounding to trailing growth habit; freely branching habit with about ten to twelve primary lateral branches each with multiple secondary and tertiary lateral branches developing per plant; pinching enhances lateral branch development; dense and bushy plant form; moderately vigorous growth habit.

*Plant height*.—About 20 cm.

*Plant diameter*.—About 25 cm.

Lateral branch description:

*Length*.—About 10 cm to 15 cm.

*Diameter*.—About 3.5 mm.

*Internode length*.—About 1 cm to 2 cm.

*Strength*.—Strong.

*Aspect*.—Initially upright then outwardly arching to trailing.

*Texture*.—Smooth, glabrous.

*Color*.—Close to 59A to 59B.

Leaf description:

*Arrangement*.—Opposite, simple.

*Length*.—About 4 cm to 5 cm.

*Width*.—About 2 cm.

*Shape*.—Ovate, elongate.

*Apex*.—Acuminate.

*Base*.—Obtuse.

*Margin*.—Serrate to dentate.

*Texture, upper and lower surfaces*.—Smooth, glabrous.

*Venation pattern*.—Pinnate; arcuate.

*Color*.—Developing leaves and fully expanded, upper surface: Close to 137A; venation, close to 137A. Developing and fully expanded leaves, lower surface: Close to 137C; venation, close to 137C.

*Petioles*.—Length: About 5 mm to 10 mm. Diameter: About 1.5 mm. Texture, upper and lower surfaces: Smooth, glabrous. Color, upper and lower surfaces: Close to 145A.

Flower description:

*Flower arrangement and habit*.—Single axillary flowers; flowers radially symmetrical; flowers initially upright and then pendulous; freely flowering habit, typically one to two flowers develop per leaf axil; at one time, about 140 to 160 flowers per plant.

*Fragrance*.—None detected.

*Natural flowering season*.—Long flowering period; flowering recurrent from mid-April through October in Northern Europe.

*Flower longevity*.—Flowers last about four to five days on the plant; flowers not persistent.

*Flower diameter*.—About 5 cm to 6 cm.

*Flower height (depth)*.—About 4.5 cm to 5 cm.

*Flower buds*.—Length: About 5 mm to 20 mm. Diameter: About 3 mm to 13 mm. Shape: Oblong. Texture: Smooth, glabrous. Color: Initially, close to 145C becoming closer to 53C with development.

*Corolla*.—Quantity of petals and arrangement: Typically twelve petals arranged in about two or three whorls; petals imbricate. Petal length: About 1.2 cm to 1.5 cm. Petal width: About 1 cm to 1.5 cm. Petal shape: Cordate. Petal apex: Obtuse. Petal base: Attenuate. Petal margin: Entire. Petal texture, upper and lower surfaces: Smooth, glabrous; velvety. Petal color: When opening and fully opened, inner surface: Close to 94B; color becoming closer to 81B with development. When opening and fully opened, outer surface: Close to 94B; color becoming closer to 81B with development.

*Calyx*.—Quantity of sepals and arrangement: Typically four sepals arranged in a single whorl and fused at the base; calyx star-shaped. Sepal length: About 2.5 cm to 3 cm. Sepal width: About 1 cm to 1.3 cm. Sepal shape: Elongate oblong; flat to reflexed. Sepal apex: Acuminate. Sepal margin: Entire. Sepal texture, upper and lower surfaces: Smooth, glabrous; velvety. Sepal color: When opening and fully opened, inner surface: Close to 57C; color does not fade with development. When opening and fully opened, outer surface: Close to 57C; color does not fade with development.

*Peduncles*.—Length: About 1 cm to 2 cm. Diameter: About 1 mm. Aspect: Arching to horizontal. Strength: Strong. Texture: Smooth, glabrous. Color: Close to 165A.

*Reproductive organs*.—Stamens: Quantity: Nine per flower. Anther size: About 1.5 mm by 2 mm. Anther shape: Oblong. Anther color: Close to 58A. Pollen amount: Abundant. Pollen color: Close to 8C. Pistils: Quantity: One per flower. Style length: About 1.5 cm to 3 cm. Style color: Close to 54D. Stigma shape: Ovate, elongated. Stigma color: Close to 18C.

*Fruits*.—Length: About 1 cm. Diameter: About 1 cm. Texture: Smooth, glabrous.

*Seeds*.—Length: About 1 mm. Diameter: About 0.5 mm. Texture: Smooth, glabrous. Color: Close to 163B.

Temperature tolerance: Plants of the new *Fuchsia* have been observed to tolerate temperatures ranging from about 4° C. to about 33° C.

Pathogen & pest resistance: Plants of the new *Fuchsia* have not been observed to be resistant to pests and pathogens common to *Fuchsia* plants.

It is claimed:

1. A new and distinct *Fuchsia* plant named 'VOLFUC 6054' as illustrated and described.

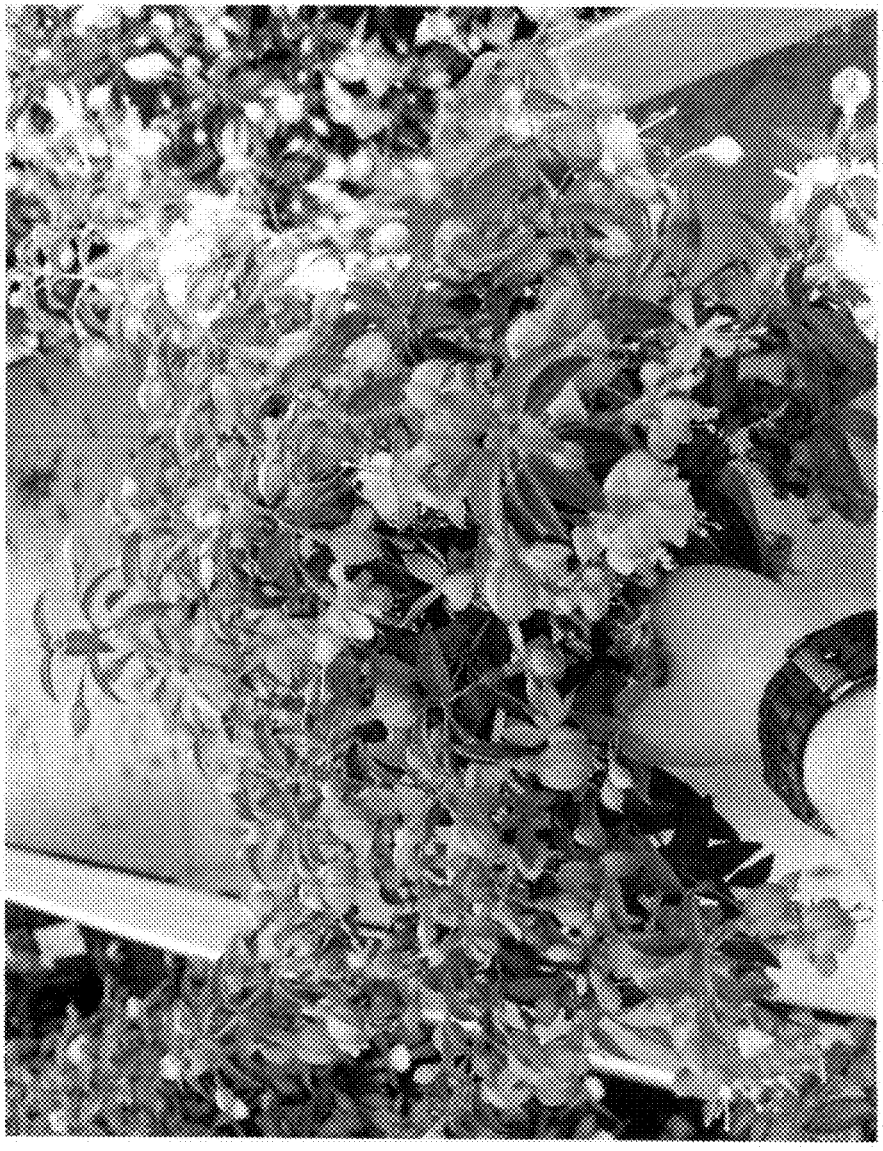

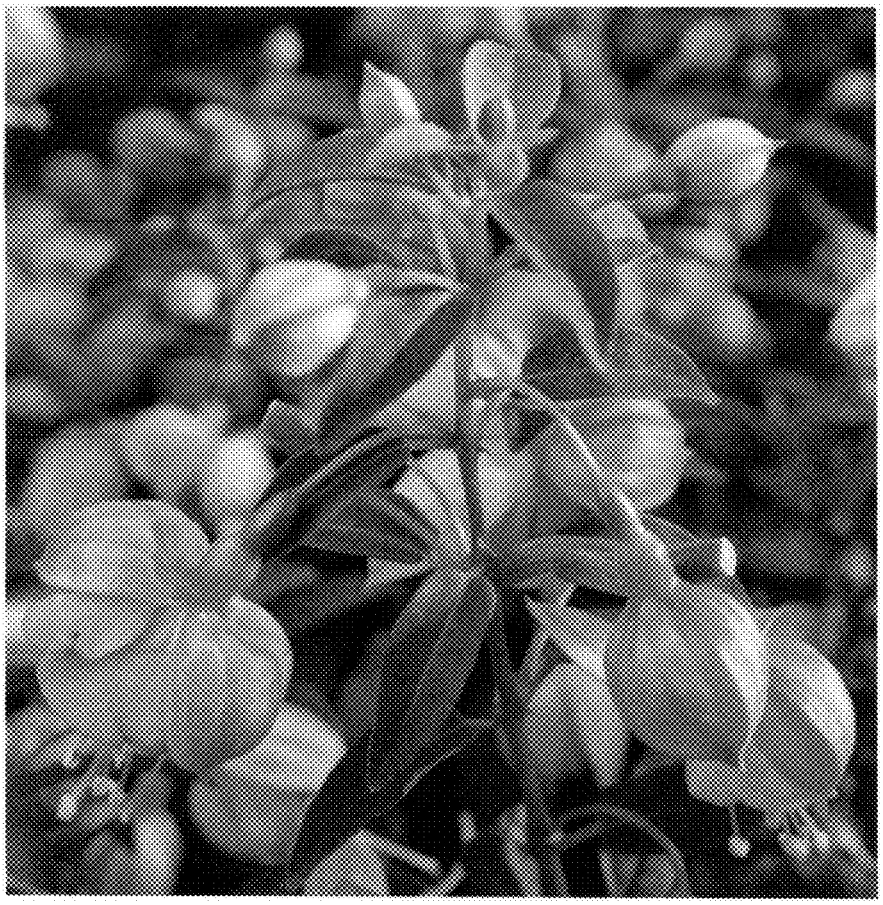

* * * * *